United States Patent [19]

Sugaya

[11] Patent Number: 4,814,279
[45] Date of Patent: Mar. 21, 1989

[54] INCUBATOR FOR CHEMICAL-ANALYTICAL SLIDE

[75] Inventor: Fumio Sugaya, Saitama, Japan

[73] Assignee: Fuji Photo Film Co., Ltd., Kanagawa, Japan

[21] Appl. No.: 26,710

[22] Filed: Mar. 17, 1987

[30] Foreign Application Priority Data

Mar. 17, 1986 [JP] Japan .................. 61-37548

[51] Int. Cl.$^4$ .................. C12M 1/36; B01L 7/00
[52] U.S. Cl. .................. 435/289; 435/284; 422/63; 422/104
[58] Field of Search .................. 435/284, 289; 422/63, 422/65, 57, 104; 436/46, 157

[56] References Cited

U.S. PATENT DOCUMENTS

| | | | |
|---|---|---|---|
| 2,942,520 | 6/1960 | Rose | 435/284 X |
| 3,726,597 | 4/1973 | Dvorak et al. | 435/284 X |
| 4,152,390 | 5/1979 | Nosco et al. | 422/57 |
| 4,219,529 | 8/1980 | Terteez et al. | 422/65 |
| 4,296,069 | 10/1981 | Smith et al. | 422/65 |
| 4,298,571 | 11/1981 | Difulvio et al. | 422/65 |
| 4,302,420 | 11/1981 | Jakulowicy | 422/63 |
| 4,303,611 | 12/1981 | Jessop | 422/104 X |
| 4,435,508 | 3/1984 | Gabridge | 435/284 |
| 4,556,639 | 12/1985 | Izawa et al. | 435/284 |
| 4,584,275 | 4/1986 | Okano et al. | 422/63 X |

Primary Examiner—Larry Jones
Attorney, Agent, or Firm—Sughrue, Mion, Zinn, Macpeak & Seas

[57] ABSTRACT

This invention relates to an incubator for chemical-analytical slides which are utilized for quantitative analysis of various components in a body fluid such as blood and urine. In an incubator having a cell into which a chemical-analytical slide is inserted and placed, a hole for photometry which is provided to a part of the slide placing-face of the above cell, a sealing member which is pushed to seal the opening for spotting of the slide, a pushing means which pushes the sealing member against the above hole for photometry, and a heating means which heats the slide, the improvement which is characterized in that the sealing member comprises a sealing part made of plastic which covers the opening for spotting and a pushing part being wear resistant which pushes the slide frame of slide. In the incubator of the invention, when a chemical-analytical slide is inserted into the cell, scratches nor abrasion are not occurred at the reverse face of the sealing member, because the position to which a strong sliding force or butting force is added is formed of a wear resistant material.

4 Claims, 4 Drawing Sheets

INCUBATOR FOR CHEMICAL-ANALYTICAL SLIDE

BACKGROUND OF THE INVENTION

1. Field of the Invention

This invention relates to an incubator for chemical-analytical slides which are utilized for quantitative analysis of various components in a body fluids such as blood and urine.

2. Description of Prior Arts

In the past, various components such as glucose, bilirubin or urea nitrogen in a body fluid were determined by placing a sample of the body fluid in a test tube and adding liquid reagent(s) prepared according to the components. However, there are some problems in this method. That is, a good deal of a body fluid sample such as human blood which is precious is necessary, its procedure is troublesome so that simple and rapid measurement is difficult, continuous measurement of many samples is difficult, and so on. In order to solve these problems, the analysis in dry process using a chemical-analytical slide cotaining all the reagents necessary for the analysis is widely utilized.

Such analytical slide is typically, as illustrated in FIG. 9, in which the chemical slide 1 is shown, composed of a multilayer analytical element 2 and a slide frame 5. The multilayer analytical element 2 is usually composed of a transparent film layer, a reagent layer, a reflecting layer and a spreading layer laminated in this order. The slide frame 5 admits this multilayer analytical element 2, and an opening for spotting a liquid sample 3 is formed on the upper side while an opening for photometry 4 is formed on the reverse side.

When a liquid sample is analyzed by using the above analytical slide 1, the liquid sample is spotted on the multilayer analytical element 2 through the opening for spotting 3. The element after spotting is incubated, for example, at 37° C. for 6 minutes to react sufficiently. Then, light is projected onto the face of the multilayer analytical element of photometric side through the opening for photometry 4, and reflected light therefrom is measured to determine the content of a particular component by colorimetry.

The analyzer for such an analytical slide is required of accuracy and simple operation. This analyzer is composed of a spotting part for the spotting of a liquid sample on to the chemical-analytical slide, an incubator to keep warm the chemical-analytical slide and to allow the proceeding of color reaction of an analyte, and a photometric part for detecting the color reaction of the chemical-analytical slide photometrically. The setting temperature and time of the incubator are generally made variable, and suitable incubational conditions are set according to the reaction system to be utilized.

As mentioned above, since chemical-analytical slides have the openings for spotting, evaporation of the liquid sample from the chemical-analytical slide during incubation is a problem. Besides, in the case of utilizing a reaction system where a color reaction is induced by the reactive gas generated by the reaction between the analyte and reagent(s), it is a problem that the analytical value lower than the true value is obtained because of effusion of a part of the reactive gas to the outside. Thereupon, the incubator was provided with a sealing member to seal the opening for spotting in order to solve the above problem. As the material of the sealing member, a plastic was employed because of slight adsorption of the reactive gas. Since the slide placing-face of the analyzer was utilized as a heater (including cooler) for maintaining temperature of the slide constant, the sealing member was reguired to press the slide to the above slide placing-face so as to exchange heat effectively. Therefore, an urging means was attached to the sealing member.

As such an incubator, the one illustrated in FIG. 10 was employed. To this incubator 6, a slide-urging unit 8 is added. 7 represents a photometric part.

A heater (not illustrated) is embedded in the upper part of the body 9 of the incubator 6, and a cell 10 into which a chemical-analytical slide 1 is inserted is bored to penetrate thereunder in a horizontal direction. A hole for photometry 11 is also bored to penetrate from the bottom face of the cell 10, which is the slide placing-face for the slide 1, to the bottom of the incubator body 9. A sealing member 13 made of plastic is mounted in the cell 10. This sealing member 13 is always urged in the direction of the hole for photometry 11 by a coil spring 12 provided between the ceiling of the cell 10 and the sealing member 13.

The photometric part 7 is located under the hole for photometry 11, and composed of light sources 14 which transmit light to the multilayer analytical elemement 2 and light receiver 15 which receives the reflected light from the multilayer analytical element 2.

The slide-pushing unit 8 inserts a chemicalanalytical slide 1 into the cell 10 at the prescribed position and draws out the inserted slide 1 from the cell 10. This slide-pushing unit 8 is composed of a sliding face 16 which is located almost the same level as the slide placing-face of the cell 10, a guide 17 which guides the chemical-analytical slide 1 and a lever 18 which pushes the chemical-analytical slide 1 into the cell 10.

When a chemical-analytical slide 1 is incubated by using such an incubator, the chemical-analytical slide 1 spotted with a liquid sample is placed on the sliding face 16, and pushed by the lever 18. By the pushing, it moves toward the cell 10, and butts against the taper face 19 of the sealing member 13. It pushes up the sealing member 13, and slides into the cell 10. Then, it stops at the prescribed position. In this state, the sealing member 13 seals the opening for spotting 3. Furthermore, it repairs curling of the slide 1, and makes flat. The chemical-analytical slide 1 is incubated at this position, and thereafter, the color formed is measured by the photometric part 7. Then, the chemical-analytical slide 1 is further pushed by the lever 18, and pushed out of the cell 10.

SUMMARY OF THE INVENTION

However, in such a coventional incubator, a problem was found that the analytical value gradually lowered according to the number of times of use.

The present inventor has found that channel-shaped scratches and projecting lines were formed on the lower surface of the sealing member by the chemical-analytical slide and the lever at its insertion and drawing out. These scratches and projections brought incomplete sealing and caused leaks of water vapor and reactive gas. Moreover, these scratches and projections increased adsorptions of these gases to lower the analytical values.

Accordingly, an object of the invention is to provide a means to ensure sealing of the opening for spotting of the chemical-analytical slide within the analyzer and obtaining exact analytical values even after a number of times of operation.

In the present invention, in order to achieve the above object, the sealing member is composed of a sealing part made of plastic which covers the opening for spotting and a pressure part being wear resistant which serves to press the slide frame.

Thus, the incubator for chemical-analytical slide of the invention is composed of a cell into which a chemical-analytical slide is inserted and placed, a hole for photometry which is provided in a portion of the slide receiving-face of the above cell, a sealing member which is urged to seal the opening for spotting of the above slide, an urging means which urges the above sealing member against the above hole for photometry, and a heating means which heats the above slide, the improvement which is characterized in that the above sealing member comprises a sealing part made of plastic which covers the above opening for spotting and a pressure part being wear resistant which is urged toward the slide frame of the above slide.

DETAILED DESCRIPTION OF THE INVENTION

The sealing part is provided in order to seal the opening for spotting of chemical-analytical slides. It is not limited that the opening is sealed by the sealing part alone, but it may be sealed partially by the pressure part. However, even in the latter case, the sealing part should cover the whole opening part. The sealing part may be of any shape, and it may be circular or square. As the material of the sealing part, a plastic adsorbing no or little reactive gas is preferable. A fluorine containing polymer is particularly suitable one.

The pressure part serves to repair curling of chemical-analytical slides by pressing the slide frame. This pressure part is wear resistant, and it is not worn. No scratch is formed at its use. As such a material, metal or ceramic is usually utilized, and metal including stainless steel, chromium plating steel and almite is preferable because of good heat conduction.

Each of the sealing part and the pressure part is enough to be located at the proper position, and either of them may be a main body. The surface of the sealing member may be in the same plane as the sliding surface of the pressure part a continuous, or the former may also be slightly indented from the sliding face.

In the incubator of the invention, when a chemical-analytical slide is inserted into the cell, neither scratches nor abrasion occurs at the surface of the sealing member confronting the analytical slide, because the position which is subject to a strong sliding force or butting force consists of a wear resistant material. Moreover, curling of the chemical-analytical slide is repaired by the pressing of the sealing member onto it, especially its hard pressure part. Accordingly, sealing of the opening for spotting of the slide is ensured even after a long period of use of the analyzer. Since the surface in contact with the reactive gas and water vapor is formed of plastic, adsorption of these gases is not a problem. As a result, exact analyses can be conducted for a long period.

EXAMPLES

Figure 1:
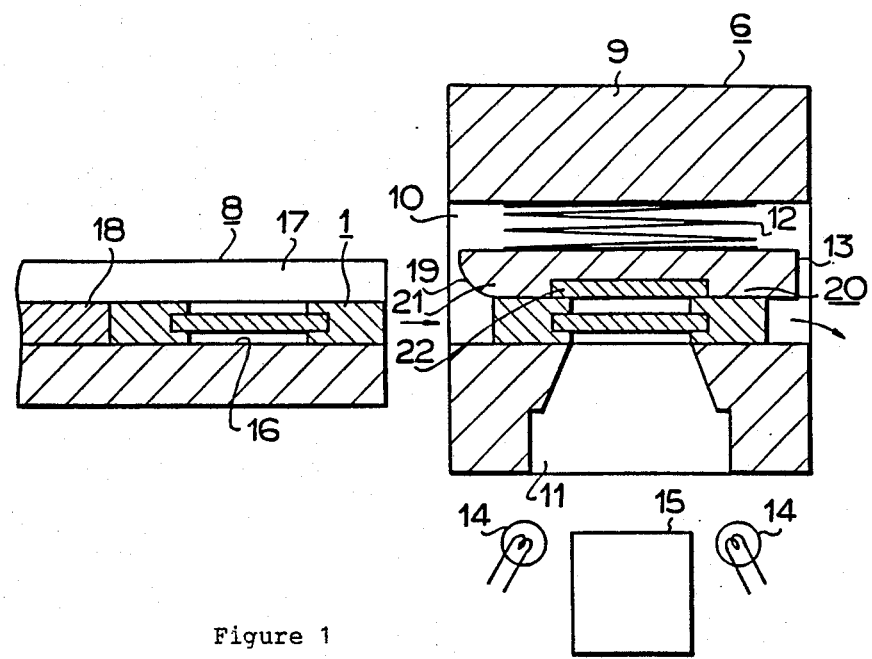
FIG. 1 is a vertical sectional view of an incubator for chemical-analytical slide embodying the invention.
Figure 2:
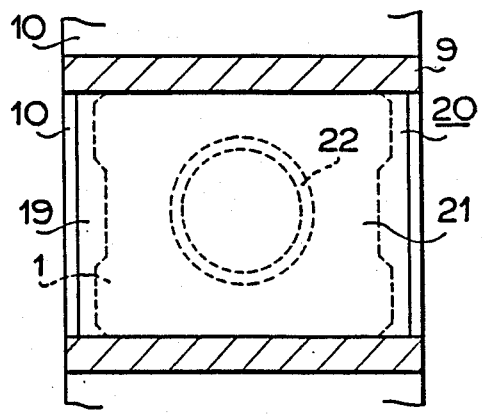
FIG. 2 is a transverse sectional view thereof.
Figure 3:
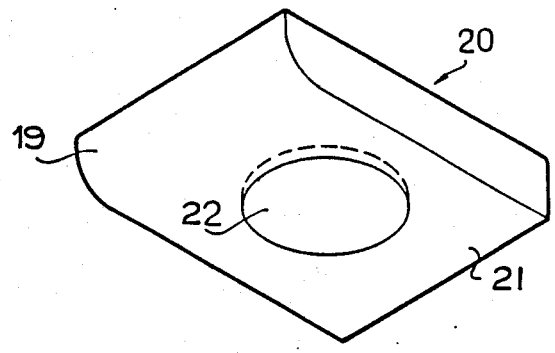
FIG. 3 is a perspective view of a sealing member observed from thereunder.

An example of the incubator for chemical-analytical slide is illustrated in FIGS. 1 to 3. FIG. 1 is a vertical sectional view of the incubator, and FIG. 2 is a transverse sectional view thereof. FIG. 3 is a perspective view of its sealing member observed from thereunder.

Figure 10:
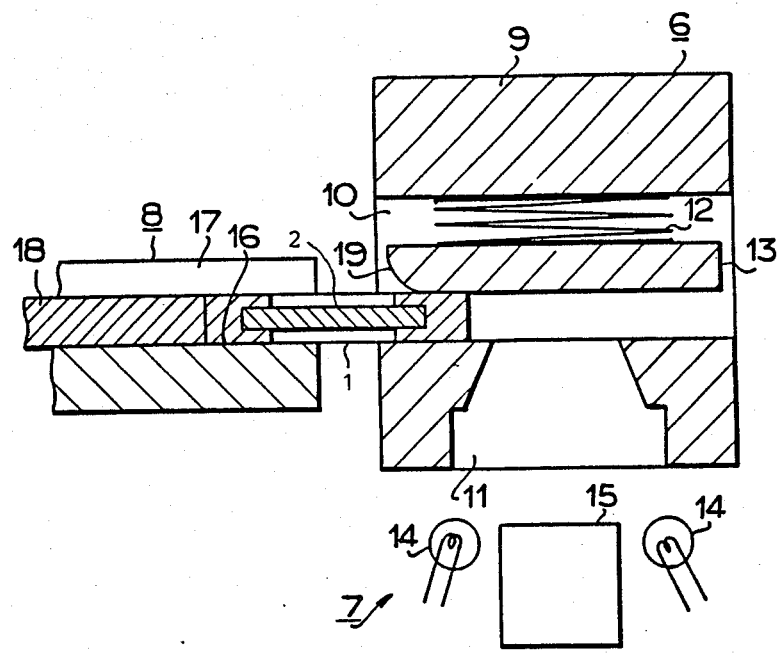
FIG. 10 is a vertical sectional view of a conventional incubator.

Except the sealing member, whole members may be identical with those of the conventional ones illustrated in FIG. 10. That is, the photometric part 7, the slide-pushing unit 8, the body 9 of the incubator 6, the cell 10, the hole for photometry 11 and the coil spring 12 are provided similarly.

The sealing member 20 has about the same contour as the cell 10, and is made of a metal such as stainless steel. The center of its lower face is cut out to form a round recess, which is filled up with a plastic disc 22, as illustrated in FIGS. 1 to 3. The metal part corresponds to the pressure part 21, and the plastic disc 22 is the sealing part.

When a chemical-analytical slide is pushed by the lever 18 of the slide-pushing unit 8, the slide 1 moves forward. The slide 1 butts against the taper face 19 of the sealing member 20, and pushes up the member 20. The slide 1 is further pushed into the cell 10, and stopped at a prescribed position. At that time, curling of the slide 1 is repaired by the pushing of the pressure part 21, and the opening for spotting 3 is sealed by the sealing part 22. Then, incubation and photometric measurement are carried out, and the slide 1 is pushed out of the cell 10 by the lever 18.

Figure 4:
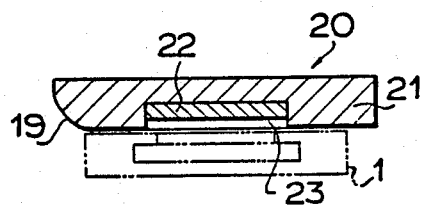
FIGS. 4 to 6 are sectional views indicating other examples of the sealing member.
Figure 5:
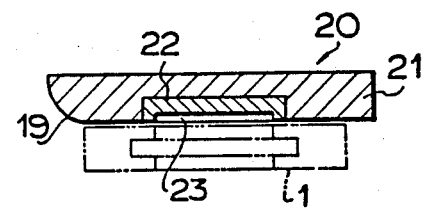
Figure 6:
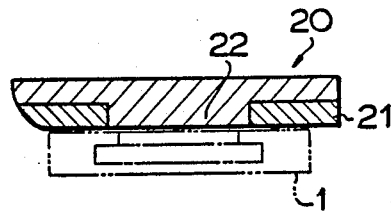

Some other examples of the sealing member employable in the incubator of the invention are shown in FIGS. 4 to 6.

In the sealing member of FIG. 4, the plastic disc 22 is slightly thinner than the depth of the recess of pressure part 21 to form a slight recess 23. This sealing member is superior in view of no touch of the sealing part 22 with the slide 1. However, it is preferably as thin as possible to the extent where the face of the plastic disc does not touch the slide frame 5. Otherwise, the space of the recess 23 and naked metal surface of narrow side wall might badly influence the color reaction.

In the sealing member of FIG. 5, the plastic disc 22 has a recess 23 which extends over almost the whole lower surface. The opening for spotting 3 can be sealed by projecting peripheral portion of the plastic disc 22.

The sealing member of FIG. 6 consists of a plastic square plate having a flat circular projection of the sealing part 22 at the center and a metal plate of the pressure part 21 having a circular hole for inserting the above projection 22. These two members are pasted to each other, and a flat lower surface is formed by the surfaces of the projection 22 and the metal plate 21.

Figure 7:
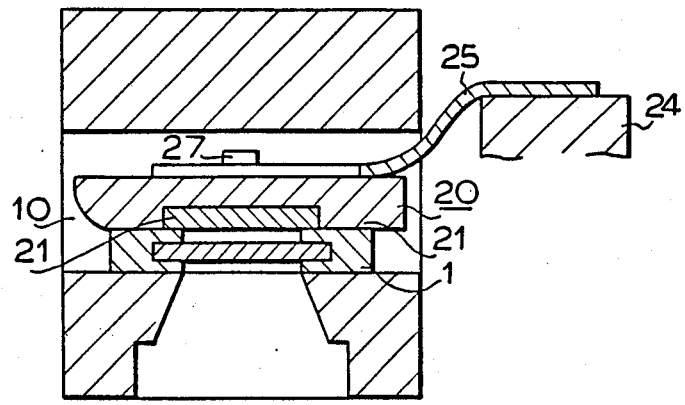
FIG. 7 is a vertical sectional view of another incubator where the pushing means is varied.
Figure 8:
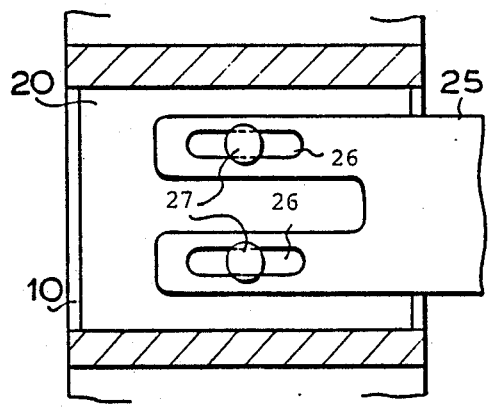
FIG. 8 is a transverse sectional view thereof.
Figure 9:
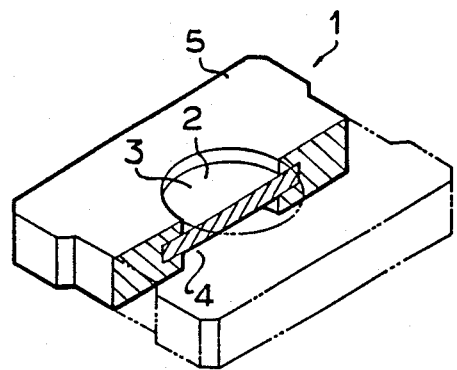
FIG. 9 is a perspective view of a chemical-analytical slide which is cut at its center.

Another example of the urging means of the sealing member is illustrated in FIGS. 7 and 8. A plate spring 25 is employed as the urging means in this example. As shown in these drawings, one end of the plate spring 25 is fixed to a base 24, and two long penetrate holes 26, 26 are provided at the other end parallel to each other. The sealing member 20 is attached to this end by screws 27, 27.

I claim:

1. In an incubator having a cell into which a chemical-analytical slide is inserted and placed, a hole for photometry which is provided in a portion of a slide receiving-face of said cell, a sealing member which is pushed to seal the opening for spotting said slide with a liquid, an urging means which urges said sealing member against said hole for photometry, and a heating means which heats said slide, the improvement which is characterized in that said sealing member comprises a sealing part made of thermoplastic polymer which completely covers said opening for spotting and a pressure part of wear resistant material which presses the slide frame of said slide toward the slide receiving-face of said cell.

2. The incubator of claim 1 wherein said pressure part is made of metal.

3. The incubator of claim 1 wherein the lower surface of said sealing part and the lower surface of said pressure part form one plane.

4. The incubator of claim 1 wherein most of or the whole lower surface of said sealing part is provided slightly indented from the lower surface of said pressure part.

* * * * *